United States Patent [19]

Riebli

[11] Patent Number: 4,968,677

[45] Date of Patent: Nov. 6, 1990

[54] SUBSTITUTED 1-ARYL-2-NAPTHOYLAMINES AND THEIR USE AS MICROBICIDES

[75] Inventor: Peter Riebli, Buckten, Switzerland

[73] Assignee: Ciba-Geigy Corporation, Ardsley, N.Y.

[21] Appl. No.: 366,972

[22] Filed: Jun. 14, 1989

[51] Int. Cl.[5] .................. C07D 233/04; C07D 211/06; C07D 295/10; A61K 31/40; A61K 31/445; A61K 31/55

[52] U.S. Cl. .................................. 514/183; 514/212; 514/319; 514/321; 514/422; 514/423; 514/452; 514/463; 514/464; 514/465; 540/450; 540/480; 540/483; 540/607; 546/205; 546/206; 546/197; 548/526; 548/539; 544/58.4; 544/161; 544/176; 544/248; 544/377; 544/391; 549/441; 564/74; 564/172

[56] References Cited

U.S. PATENT DOCUMENTS 4,499,094 2/1985 Dubroeucq et al. .................. 514/311

FOREIGN PATENT DOCUMENTS 3710717 10/1988 Fed. Rep. of Germany .

OTHER PUBLICATIONS

Indian J. Pharm. Sci., 47(1), 12–15 (1985).
J. Chem. Soc. Perkin Trans. I, 1360–1366 (1978).
Chem. Abstract, vol. 110:1352494 (1989), Curtze et al., DE 3,710,717.

Primary Examiner—Mukund J. Shah
Assistant Examiner—Philip I. Datlow
Attorney, Agent, or Firm—Edward McC. Roberts; George R. Dohmann

[57] ABSTRACT

1-Aryl-2-naphthoylamines of formula I are described

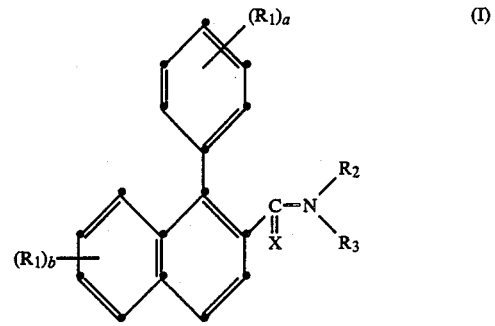

wherein $R_1$ is halogen, nitro, cyano, $C_1$–$C_6$alkyl that is unsubstituted or mono- or poly-substituted by halogen and/or $C_1$–$C_3$alkoxy, or is $C_3$–$C_6$cycloalkyl, $OR_4$, $NR_5R_6$, $CO_2R_5$, $CONR_5R_6$ or $NHCOR_7$, or wherein two adjacent positions in the nucleus are bridged by a methylenedioxy or ethylenedioxy group that is unsubstituted or mono- or poly-substituted by fluorine, wherein further $R_4$ is hydrogen or $C_1$–$C_6$alkyl that is unsubstituted or substituted by $C_1$–$C_3$alkoxy or mono- or poly-substituted by halogen, or is $C_3$–$C_4$alkenyl, 2-propynyl, 3-halo-2-propynyl,

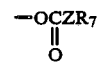

or $COR_7$, each of $R_5$ and $R_6$, independently of the other, is H or $C_1$–$C_4$alkyl, $R_7$ is $C_1$–$C_4$alkyl and Z is O or NH, a and b denote the number of occupied positions in the respective 6-membered ring, and a is a number from 1 to 3 and b is a number from 0 to 3, the individual groups $R_1$ being identical or different when the sum of a and b is greater than 1, X is O, S or NH, each of $R_2$ and $R_3$, independently of the other, is $C_1$–$C_6$alkyl that is unsubstituted or substituted by $C_1$–$C_4$alkoxy, halogen or by cyano, or is $C_3$–$C_7$cycloalkyl, $C_3$–$C_7$alkenyl or the radical

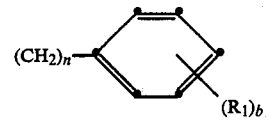

wherein n is 0 or 1, or $R_2$ and $R_3$ are also together a $C_4$–$C_7$alkylene chain that together with the nitrogen atom may form a heterocycle that is unsubstituted or mono- or di-substituted by $C_1$–$C_4$alkyl, it being possible for one of the methylene groups in this chain to be replaced by O, S or $NR_7$, and for $R_2$ also to be hydrogen.

The compounds of formula I have microbicidal activity and can be used advantageously for plant protection.

6 Claims, No Drawings

SUBSTITUTED 1-ARYL-2-NAPTHOYLAMINES AND THEIR USE AS MICROBICIDES

The present invention relates to substituted 1-aryl-2-naphthoylamines, to the preparation thereof and to microbicidal compositions that contain at least one of these compounds as active ingredient. The invention further relates to the preparation of said compositions and to the use of the novel active ingredients and compositions for controlling pathogenic microorganisms, especially phytopathogenic fungi.

The compounds of the invention are of the general formula I

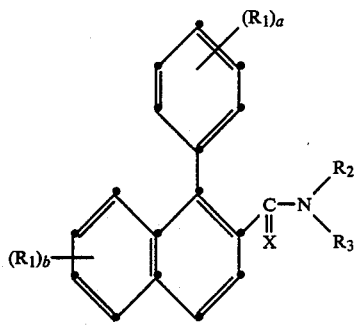

wherein $R_1$ is halogen, nitro, cyano, $C_1$-$C_6$alkyl that is unsubstituted or mono- or poly-substituted by and/or $C_1$-$C_3$alkoxy, or is $C_3$-$C_6$cycloalkyl, $OR_4$, $NR_5R_6$, $CO_2R_5$, $CONR_5R_6$ or $NHCOR_7$, or wherein two adjacent positions in the nucleus are bridged by a methylenedioxy or ethylenedioxy group that is unsubstituted or mono- or poly-substituted by fluorine, wherein further $R_4$ is hydrogen or $C_1$-$C_6$alkyl that is unsubstituted or substituted by $C_1$-$C_3$alkoxy or mono- or poly-substituted by halogen, or is $C_3$-$C_4$alkenyl, 2-propynyl, 3-halo-2-propynyl,

or $COR_7$, each of $R_5$ and $R_6$, independently of the other, is H or $C_1$-$C_4$alkyl, $R_7$ is $C_1$-$C_4$alkyl and Z is O or NH, a and b denote the number of occupied positions in the respective 6-membered ring, and a is a number from 1 to 3 and b is a number from 0 to 3, the individual groups $R_1$ being identical or different when the sum of a and b is greater than 1, X is oxygen, sulfur or NH, each of $R_2$ and $R_3$, independently of the other, is $C_1$-$C_6$alkyl that is unsubstituted or substituted by $C_1$-$C_4$ alkoxy, halogen or by cyano, or is $C_3$-$C_7$ cycloalkyl, $C_3$-$C_7$ alkenyl or the radical

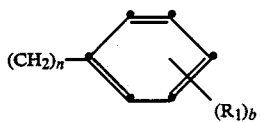

wherein n is 0 or 1, or $R_2$ and $R_3$ are also together a $C_4$-$C_7$alkylene chain that together with the nitrogen atom may form a heterocycle that is unsubstituted or mono- or di-substituted by $C_1$-$C_4$ alkyl, it being possible for one of the methylene groups in this chain to be replaced by O, S or $NR_7$, and for $R_2$ also to be hydrogen; including the addition salts of compounds of formula I.

Depending on the number of carbon atoms indicated, the term alkyl on its own or as a component of another substituent is used to mean, for example, one of the following groups: methyl, ethyl, propyl, butyl, pentyl, hexyl etc. and the isomers thereof, e.g. isopropyl, isobutyl, tert.-butyl, isopentyl etc.. Cycloalkyl may be, for example, cyclopropyl, cyclopentyl or cyclohexyl. Haloalkyl denotes a mono- to per-halogenated alkyl substituent, e.g. $CH_2Cl$, $CHCl_2$, $CCl_3$, $CH_2Br$, $CHBr_2$, $CBr_3$, $CH_2F$, $CHF_2$, $CF_3$, $CCl_2F$, $CCl_2$-$CHCl_2$, $CH_2CH_2F$, $CI_3$ etc.. Throughout this specification, halogen is used to mean fluorine, chlorine, bromine or iodine, preferably fluorine or chlorine.

When a methylenedioxy group or an ethylenedioxy group is present in one of the rings, two adjacent positions are accordingly occupied.

The compounds of formula I are oils, resins or predominantly crystalline solids that are stable under normal conditions and are distinguished by extremely valuable microbicidal properties. They can be used, for example in the agricultural sector or related fields, preventively and curatively for controlling phytopathogenic microorganisms. The active ingredients of formula I are distinguished by a high fungicidal activity and unproblematical use over a wide concentration range. No damage to the treated plants is observed.

1-Phenyl-4-hydroxy-2-naphthoylamines of the formula

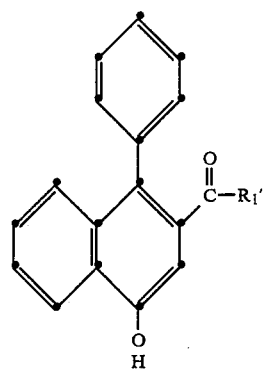

where $R_1$ is dimethylamino, anilino, 4-chloroanilino, 4-methylanilino or benzylamino, are known from the literature as pharmaceuticals (Indian J, Pharm. Sci. 1985 47(1) 12-15; C.A. 103 25, 205882f (1985). Some of these compounds have an antiinflammatory action.

1-Acetoxy- and 1-hydroxy-3-morpholinocarbonyl-4-phenylnaphthalene of the formula

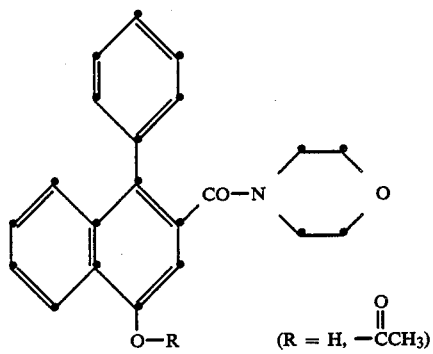

(R = H, —$\overset{\text{O}}{\underset{\|}{\text{C}}}$CH$_3$)

are described in J. Chem. Soc. Perkin Trans. 1 1978 (11), 1360–1366; C.A. 90 (9), 71721e (1979). Commercially useful properties of these compounds are not indicated.

No 1-aryl-2-naphthoylamines having microbicidal activity are known from the literature.

The object of the present invention is to provide novel microbicidally active ingredients. It has surprisingly been found that the compounds of formula I have pronounced microbicidal activity.

Preferred compounds of formula I are those wherein $R_1$ is halogen, nitro, $C_1$–$C_6$alkyl, $C_3$–$C_6$cycloalkyl, methylenedioxy, mono- or di-fluoromethylenedioxy, unsubstituted ethylenedioxy or ethylenedioxy mono- or poly-substituted by fluorine, or is $OR_4$ or $NR_5R_6$, wherein $R_4$ is hydrogen or $C_1$–$C_3$alkyl that is unsubstituted or mono-substituted by $C_1$–$C_3$alkoxy or mono- to penta-substituted by halogen, each of $R_5$ and $R_6$, independently of the other, is H or $C_1$–$C_4$alkyl, a is the number 2 or 3, b is 0 or 1, and X is O or S, while each of $R_2$ and $R_3$, independently of the other, is phenyl, 4-chlorophenyl, or $R_2$ and $R_3$ are also together a $C_4$–$C_7$alkylene chain that together with the nitrogen atom may form a heterocycle that is unsubstituted or mono- or di-substituted by $C_1$–$C_4$alkyl, it being possible for one of the methylene groups in the chain to be replaced by O, S or $NR_7$.

Of this group of compounds, attention is drawn to those in which $R_1$ is methyl, chlorine, methoxy, ethoxy, difluoromethoxy, methylenedioxy, difluoromethylenedioxy, ethylenedioxy, nitro, or mono- or di-methylamino, and $R_2$ and $R_3$ together with their common nitrogen atom form the radical

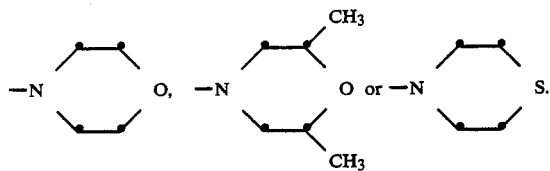

Compounds of interest from this group are those in which $R_1$ is methoxy or methylenedioxy and a is the number 2.

Among the last-mentioned group, those compounds in which X is oxygen are prominent as microbicides.

An especially effective individual compound from this group is the compound of formula Ia:

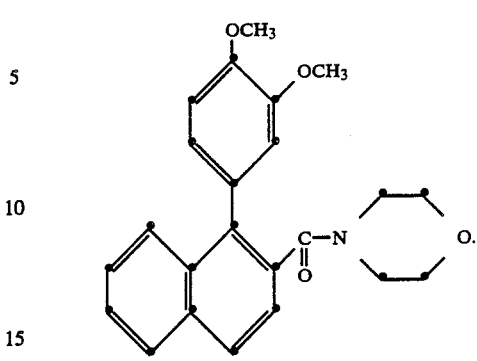

Of the compounds of formula I in which $R_1$ is methoxy or methyl and a is the number 2 or 3 and b is 0, compounds to be given prominence as microbicides are those in which X is sulfur.

An individual representative of this group is the compound of formula Ib:

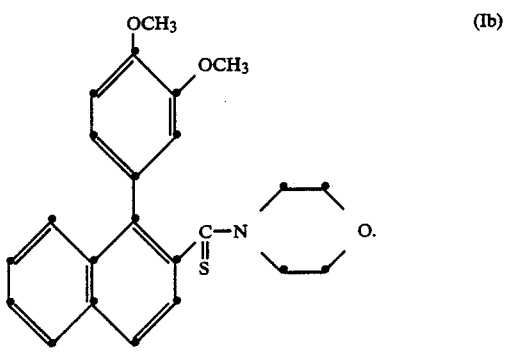

Of the compounds of formula I in which $R_1$ is halogen, nitro, $C_1$–$C_6$alkyl, $C_1$–$C_3$alkoxy, $C_3$–$C_6$cycloalkyl, methylenedioxy, mono- or di-fluoromethylenedioxy, unsubstituted ethylenedioxy or ethylenedioxy mono- or poly-substituted by fluorine, or $NR_5R_6$ wherein each of $R_5$ and $R_6$, independently of the other, is H or $C_1$–$C_4$alkyl, a is the number 2 or 3, and b is 0 or 1, and X is O or S, and each of $R_2$ and $R_3$, independently of the other, is hydrogen, unsubstituted $C_1$–$C_6$alkyl or $C_1$–$C_6$alkyl substituted by $C_1$–$C_4$alkoxy, halogen or cyano, or $C_3$–$C_7$alkenyl, or is phenyl or 4-chlorophenyl, or $R_2$ and $R_3$ are also together a $C_4$–$C_7$alkylene chain that together with the nitrogen atom may form a heterocycle that is unsubstituted or mono- or di-substituted by $C_1$–$C_4$alkyl, it being possible for one of the methylene groups in the chain to be replaced by O, S or $NR_7$, there are preferred as microbicides those of formula Ic

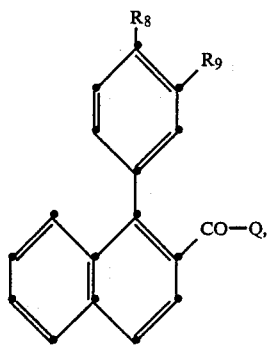
(Ic)

wherein either each of R₈ and R₉ is a methoxy radical or R₈ and R₉ together are a methylenedioxy radical and Q represents the following radicals:

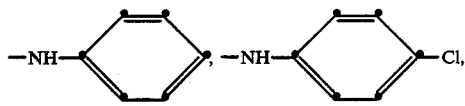

—N(CH₃)₂, —(C₂H₅)₂, —(C₂H₄OCH₃)₂,

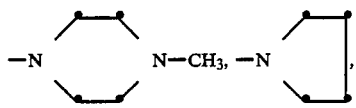

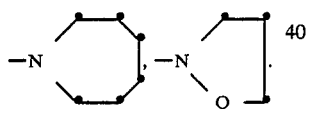

There may be mentioned as an individual representative of this group inter alia the compound of formula Id:

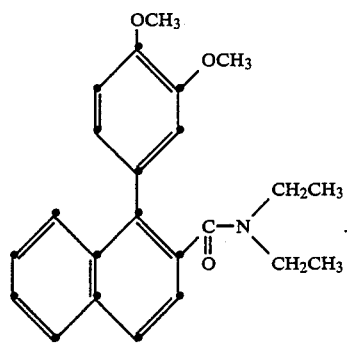
(Id)

Of the compounds of formula I, there should also be given prominence as valuable microbicides those of formula Ie

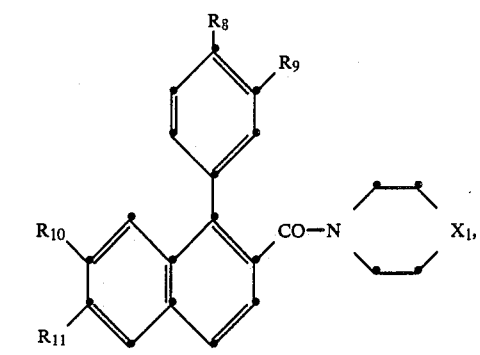
(Ie)

wherein either each of R₈ and R₉ is methoxy or R₈ and R₉ together are methylenedioxy, and each of R₁₀ and R₁₁ is methoxy or R₁₀ and R₁₁ together are methylenedioxy, or R₁₁ may furthermore be chlorine, nitro, amino or acetylamino whilst R₁₀ is hydrogen, and X₁ is O or S.

The compounds of formula I are prepared in accordance with the invention by converting an amine of formula II $$HN\begin{smallmatrix}R_2\\R_3\end{smallmatrix}$$ (II)

wherein R₂ and R₃ are as defined for formula I,
(a) with a naphthoic acid derivative of formula III

(III)

wherein R₁, a and b are as defined for formula I and Y is OH, halogen or C₁–C₄alkoxy, into a compound of formula I'

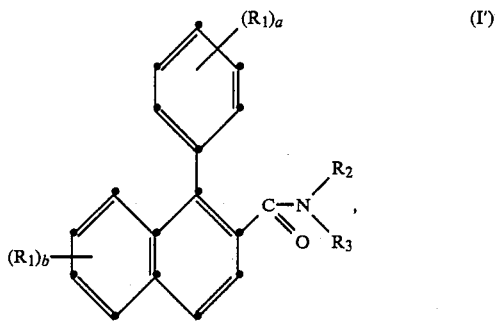
(I')

and, if desired, converting the compound I' with phosphorus petasulfide into a thiocarbonamide of formula I"

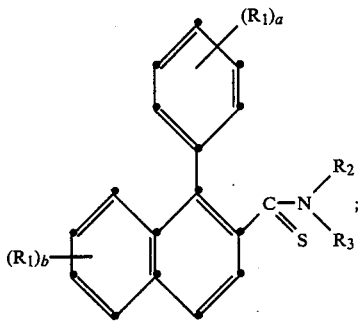

or, to obtain compounds of formula I wherein X is NH, (b) with an imino ester of formula IV

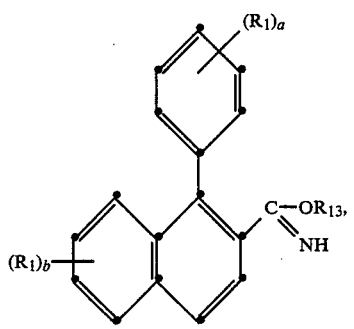

wherein $R_1$, a and b are as defined for formula I and $R_{13}$ is $C_1$–$C_4$alkyl, into a compound of formula I'''

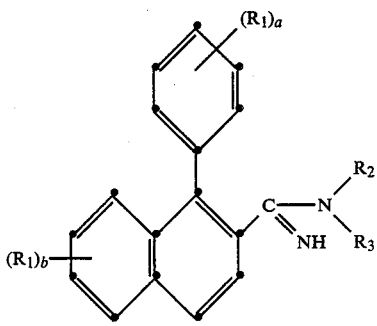

The preparation of compounds of formula I' involves the acylation of an amine of formula II with a carboxylic acid derivative or with a carboxylic acid of formula III, the latter being employed preferably in the presence of an agent that activates the acid or removes the elements of water.

Examples of suitable acid-activating and/or water-removing agents are a chloroformic acid ester such as chloroformic acid ethyl ester, or phosphorus pentoxide, N,N'-dicyclohexylcarbodiimide, N,N'-carbonyldiimidazole or N,N'-thionyldiimidazole.

The reaction is advantageously carried out in a solvent or a mixture of solvents, such as methylene chloride, chloroform, carbon tetrachloride, ether, tetrahydrofuran, dioxane, benzene, toluene, acetonitrile or dimethylformamide, where appropriate in the presence of an inorganic base, such as sodium carbonate, or a tertiary organic base, such as triethylamine or pyridine, which may simultaneously serve as solvent, and, where appropriate, in the presence of an acid-activating agent at temperatures of from −25° C. to 150° C., preferably, however, at temperatures of from −10° C. to the boiling temperature of the reaction mixture. It is not necessary to isolate a reactive derivative of a compound of the general formula III which may have formed in the reaction mixture; and the reaction may also be carried out using the compound of general formula II in excess as solvent.

In order to prepare such compounds of formula I'' (thioamides), the corresponding amides are reacted in an inert solvent with phosphorus pentasulfide. In some cases, $P_2S_5$ can be used advantageously in the presence of $K_2S$ or $K_2(S_x)$.

Suitable solvents are, for example, toluene, xylene and benzene. The reaction temperature is from 0° C. to the boiling temperature of the reaction mixture; however, in general, a temperature of 120° C. should not be exceeded.

In order to prepare such compounds of formula I''' (amidines), corresponding imino esters are reacted with amines of formula II.

The reaction is carried out in an inert solvent, such as ether or tetrahydrofuran, at temperatures of approximately from 0° to 100° C.

Carboxylic acids of formula III are in some cases known or can be prepared by customary methods (J. Org. Chem. 1981 46 3881–3886; J. Org. Chem. 1964 29 1757–1762; Synthesis 1983 105–107). Imino esters of formula IV can be obtained from the corresponding nitriles by addition of a $C_1$–$C_4$alkanol in the presence of HCl.

The amines of formula II are generally known.

The compounds of formula III wherein Y is halogen or $C_1$–$C_4$alkoxy can be prepared from the corresponding carboxylic acids.

The carboxylic acids of formula IIIa

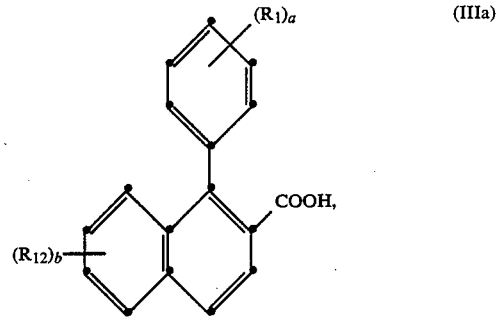

wherein $R_1$ is fluorine, chlorine or $C_1$–$C_{3alkoxy}$ or $OR_4$, and $R_1$, $R_4$ and a and b are as defined for formula I, can be prepared by reacting suitable organometal compounds, e.g. Grignard compounds or lithium compounds, with carbonic acid. The organometal compounds themselves can be prepared by known methods by metallating the corresponding bromine compounds of formula VIII with a suitable metal, such as activated magnesium, or with a metal compound, such as butyllithium:

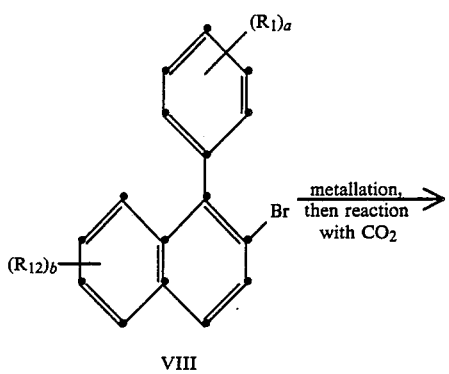

VIII

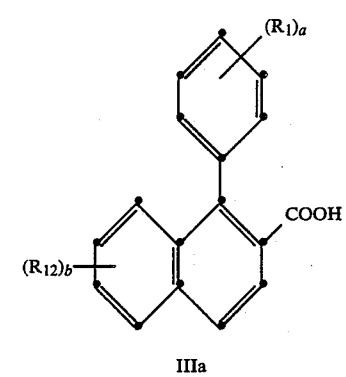

IIIa

The bromine compounds of formula VIII can in turn be prepared by dehydrogenation of the corresponding 3,4-dihydronaphthalenes of formula VI. The dehydrogenation can be carried out according to known methods, e.g. by reaction with dehydrogenation agents, such as sulfur, or quinones, preferably, 2,3-dichloro-5,6-dicyano-1,4-benzoquinone (Chem. Rev. 78 317 1978). The compounds of formula VI themselves can be prepared by reacting dihydronaphthalenes of formula V with suitable brominating agents, e.g. pyridinium hydrobromide perbromide (J. Med. Chem. 29 2053–2059, 1986)

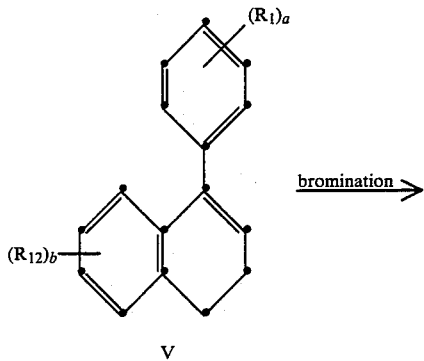

V

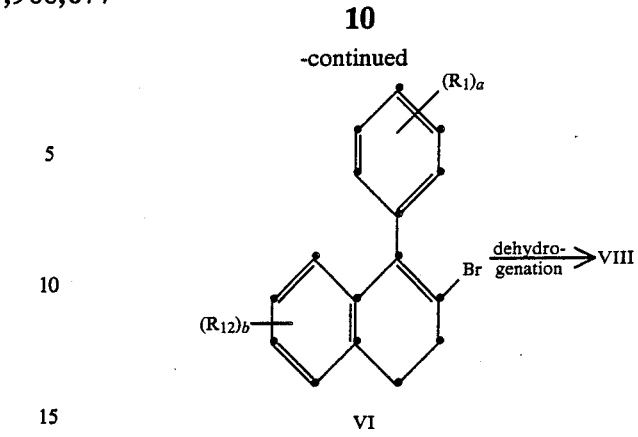

VI

By varying the analogous synthesis steps, the 3,4-dihydronaphthalene compounds of formula VI can first be converted via the metal compounds with carbonic acid into the 3,4-dihydronapthalenecarboxylic acids of formula VII which are finally dehydrogenated to give the compounds of formula IIIa:

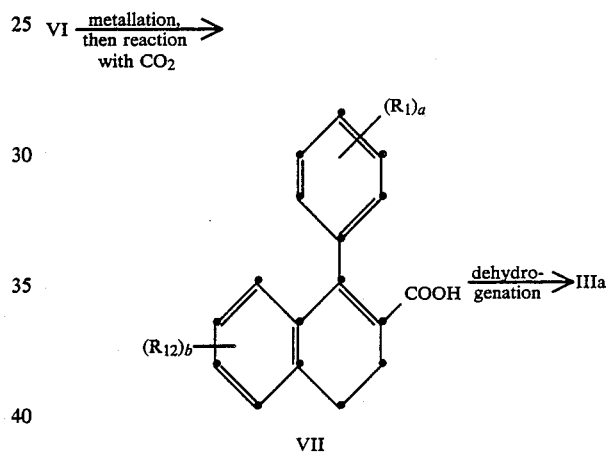

VII

The compounds of formula V are in some cases known or can be prepared by known methods [Tetrahedron 38 2403–2410, (1982), Aust. J. Chem. from 34, 115–129 (1981)].

The bromonaphthalenecarboxylic acids of formula IIIc

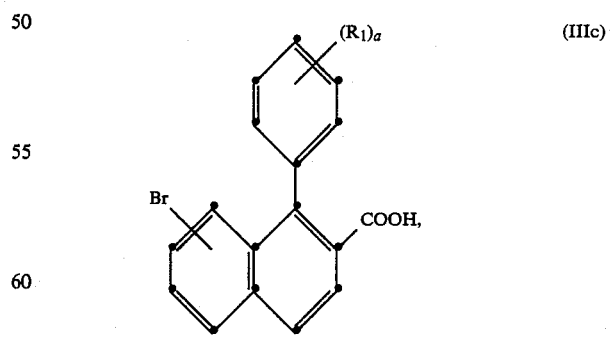

wherein a and $R_1$ are as defined for formula I, can be prepared starting from the corresponding nitrated naphthalene carboxylic acids of formula IIIb according to a known reaction sequence (reduction. diazotisation, Sandmeyer reaction)

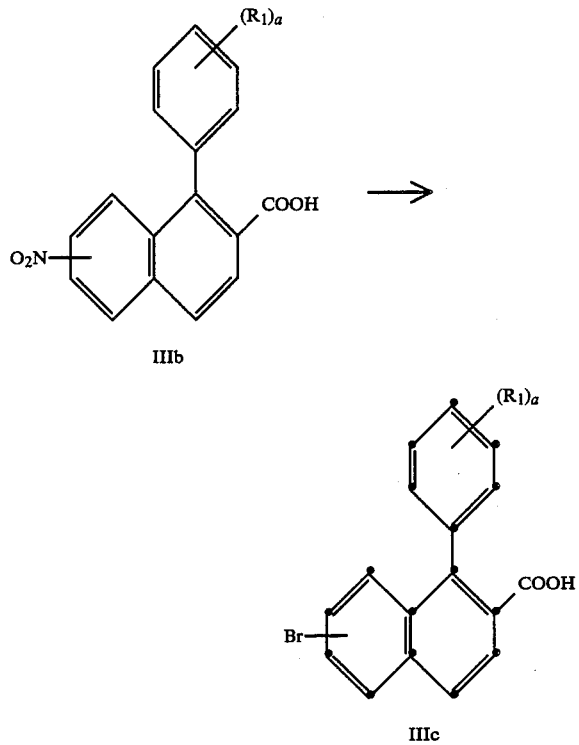

IIIb

IIIc

Surprisingly, it has now been found that the compounds of formula I of the invention have, for practical field application purposes, a very advantageous biocidal spectrum of action against pathogenic microorganisms, especially phytopathogenic fungi and bacteria. They have very advantageous curative, systemic and, in particular, preventive properties, and can be used for protecting numerous cultivated plants. With the compounds of formula I it is possible to inhibit or destroy the phytopathogenic microorganisms which occur in plants or in parts of plants (fruit, blossoms, leaves, stems, tubers, roots) in different crops of useful plants, while at the same time the parts of the plants which grow later are also protected from attack by such microorganisms.

The compounds of the invention are effective, for example, against the phytopathogenic fungi belonging to the following classes: Ascomycetes, e.g Erysiphe, Sclerotinia, Fusarium, Monolinia, Helminthosporium; Basidiomycetes, e.g. Puccinia, Tilletia, Rhizoctonia; and, in particular, against the Oomycetes belonging to the class of the Phycomycetes such as Phytophthora, Plasmopara, Peronospora, Pythium. As plant protective agents, the compounds of formula I can also be used against important pathogenic fungi from the family of the Fungi imperfecti, e.g. against Cercospora, Pyricularia and Botrytis. The compounds furthermore have a systemic action. In addition, the compounds of formula I can be used successfully for the protection of perishable goods of vegetable or animal origin. They control mould fungus, such as Penicillium, Aspergillus, Rhizopus, Fusarium, Helminthosporium, Nigrospora and Alternaria, and also bacteria, such as butyric acid bacteria and yeasts, such as Candida. These active ingredients futhermore exhibit outstanding activity against soil-borne and seed-borne fungi.

The compounds of formula I can also be used as dressing agents for protecting seeds (fruit, tubers, grains) and plant cuttings against fungus infections as well as against phytopathogenic fungi which occur in the soil, being especially distinguished as dressing agents for cereals in the control of fungal organisms, for example species of Fusarium, Helminthosporium and Tilletia.

The invention accordingly relates also to microbicidal compositions and to the use of the compounds of formula I for controlling phytopathogenic microorganisms, in particular phytopathogenic fungi, or for protecting plants and stored goods of vegetable or animal origin from attack by such microorganisms.

Target crops to be protected within the scope of this invention comprise e.g. the following species of plants: cereals (wheat, barley, rye, oats, rice, sorghum and related crops), beet (sugar beet and fodder beet), pomes, drupes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconut, castor oil plants, cocoa beans, groundnuts), cucumber plants (pumpkins, cucumbers, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (Compositae).

The compounds of formula I are normally applied in the form of compositions and can be applied to the crop area or plant to be treated, simultaneously or in succession, with further compounds. These further compounds can be fertilisers or micronutrient donors or other preparations that influence plant growth. They can also be selective herbicides, insecticides, fungicides, bactericides, nematicides, molluscicides or mixtures of several of these preparations, if desired together with further carriers, surfactants or application-promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers. Particularly advantageous application-promoting adjuvants which are able to reduce substantially the rate of application are also natural (animal or vegetable) or synthetic phospholipids of the series of the cephalins and lecithins, e.g. phosphatidyl ethanolamine, phosphatidyl serine, phosphatidyl glycerol or lysolecithin.

A preferred method of applying a compound of formula I, or an (agro)chemical composition which contains at least one of said compounds, is foliar application. The number of applications and the rate of application depend on the risk of infestation by the corresponding pathogen (species of fungus). However, the compounds of formula I can also penetrate the plant through the roots via the soil (systemic action) if the locus of the plant is impregnated with a liquid formulation, or if the compounds are applied in solid form to the soil, e.g. in granular form (soil application). The compounds of formula I may, however, also be applied to seeds (coating) by impregnating the seeds either with a liquid formulation of a compound of formula I, or coating them with a solid formulation. In special cases, further types of application are also possible, e.g. selective treatment of the plant stems or buds.

The compounds of formula I are used in unmodified form or, preferably, together with the adjuvants conventionally employed in the art of formulation, and are therefore formulated in known manner e.g. into emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethylene glycol monomethyl ether, ketones such as cyclohexanone, strongly polar solvents such as N-methyl-2-pyrrolidone, dimethyl sulfoxide or dimethylformamide, as well as vegetable oils or epoxidised vegetable oils, or soybean oil; or water.

As solid carriers e.g. for dusts and dispersible powders, it is possible to use calcite, talcum, kaolin, montrorillonite or attapulgite, highly dispersed silicic acid or absorbent polymers. Suitable granulated adsorptive carriers are pumice, broken brick, sepiolite or bentonite; and suitable nonsorbent carriers are, for example, calcite or dolomite. Pulverised plant residues can also be used.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

The surfactants customarily employed in the art of formulation are described inter alia in the following publications:
"McCutcheon's Detergents and Emulsifiers Annual" MC Publishing Corp., Ridgewood, N.J., 1980; Sisley and Wood, "Encyclopedia of Surface Active Agents", Chemical Publishing Co., Inc. New York, 1980.

The agrochemical compositions usually contain 0.1 to 99%, preferably 0.1 to 95%, of a compound of formula I, 99.9 to 1%, preferably 99.9 to 5%, of a solid or liquid adjuvant, and 0 to 25%, preferably 0.1 to 25%, of a surfactant.

Whereas commercial products will preferably be formulated as concentrates, the end user will normally employ dilute formulations.

The present invention relates to such (agro)chemical compositions.

The following Examples serve to illustrate the invention without implying any limitation of the scope thereof (percentages and parts are by weight; temperatures are in degrees Celsius).

1. PREPARATION EXAMPLES

P.1: Preparation of
1-(3,4-dimethoxyphenyl)-2-naphthoic acid morpholide
(active ingredient, comp. no. 1.1, Table 1).

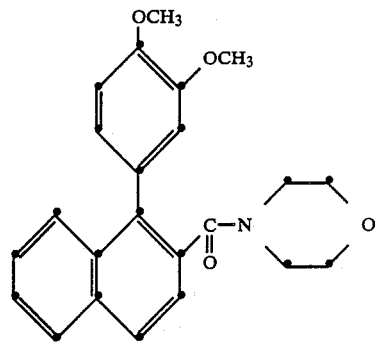

12.3 g of 1-(3,4-dimethoxyphenyl)-2-naphthoic acid introduced into 70 ml of toluene, and 4.8 g of thionyl chloride are added thereto. The reaction mixture is heated to boiling point and stirred under reflux for 16 hours. Then, at 50°, 7.0 g of morpholine are added dropwise, the reaction mixture is stirred under reflux for a further 4 hours, then diluted at reduced temperature with 100 ml of toluene and washed three times with 200 ml of water each time. The organic phase is dried over sodium sulfate and filtered, and the solvent is evaporated off in vacuo. For purification, the oily residue is chromatographed over a column of silica gel using ethyl acetate. The title compound is obtained in the form of a yellow oil which solidifies upon being left to stand. M.p. 161°–163°.

P.2: Preparation of
2-(4,4-dimethyl-4,5-dihydro-1,3-oxazol-2-yl)-1-(3,4-dimethoxyphenyl)-naphthalene (intermediate).

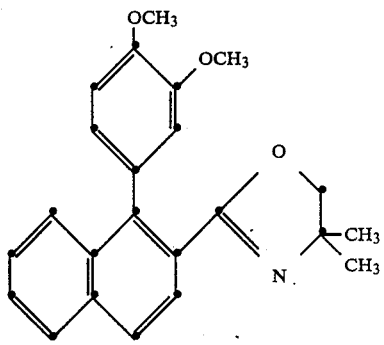

21.3 g of 2-(4,4-dimethyl-4,5-dihydro-1,3-oxazol-2-yl)-1-methoxynapththalene are added dropwise at 50° to 25.5 g of Grignard reagent prepared from 23.2 g of 4-bromo-veratrol and 2.5 g of magnesium in 50 ml of tetrahydrofuran, and the red reaction mixture is heated to boiling point and stirred for 4 hours under reflux; then, at reduced temperature, ~200 ml of saturated ammonium chloride solution are added and the whole is extracted three times with 100 ml of ether each time. The ethereal phases are combined, washed twice with 200 ml of water each time and dried over sodium sulfate, and the solvent is evaporated off in vacuo. For purification, the oily residue is chromatographed over a column of silica gel using hexane/ethyl acetate 1:1. The compound is obtained in the form of a yellow oil $n_D^{24.5}$:1.6158.

P.3: Preparation of 1-(3,4-dimethoxyphenyl)-2-naphthoic acid (intermediate)

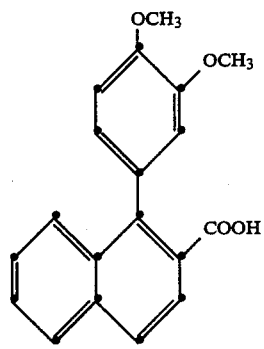

16.0 g of the 2-(4,4-dimethyl-4,5-dihydro-1,3-oxazol-2-yl)-1-(3,4-dimethoxyphenyl)-naphthalene prepared in P.2 are boiled for 8 hours in 40 ml of 3N hydrochloric acid. The two-phase mixture is then cooled to room temperature and the phases are separated. The heavy phase is stirred under reflux for 40 hours with 40 ml of 20% methanolic (methanol/H$_2$O 1:1) sodium hydroxide solution, the methanol is distilled off, and the aqueous residue is diluted with 100 ml of water and extracted three times with 100 ml of ethyl acetate each time. The aqueous phase is adjusted to pH 1 with concentrated hydrochloric acid. The resulting crystals are filtered off with suction, washed twice with 100 ml of water each time and dried in a vacuum drying cabinet at 60° C. M.p.>215° C.

P.4: Preparation of 1-(3,4-dimethoxyphenyl)-6-chloro-2-naphthoic acid morpholide (comp. no. 3.1, Table 3).

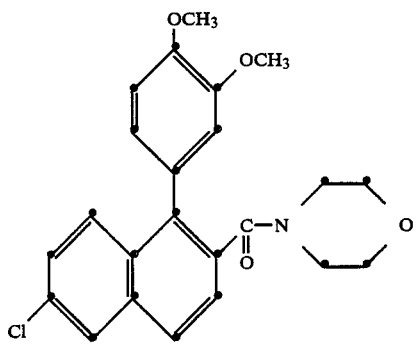

6.9 g of 1-(3,4-dimethoxyphenyl)-6-chloro-2-naphthoic acid are introduced into 50 ml of toluene, and 2.4 g of thionyl chloride are added thereto. The reaction mixture is heated to boiling point and then stirred for 5 hours under reflux. Then, at ~50°, 4.0 g of morpholine are added dropwise, and the mixture is again heated to boiling point and stirred for a further 3 hours under reflux. After cooling to room temperature, the reaction mixture is diluted with 100 ml of toluene, and the organic phase is washed three times with 250 ml of water each time, dried over sodium sulfate and filtered, and the solvent is evaporated off in vacuo. For purification, the oily residue is chromatographed over a column of silica gel using ethyl acetate. The title compound is obtained in the form of beige crystals. M.p. 157°–159°.

P.5: Preparation of 1-(3,4-dimethoxyphenyl)-6-chloro-2-naphthoic acid (intermediate)

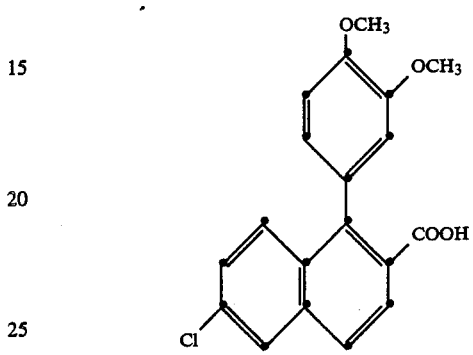

Dry carbon dioxide from −5° to 0° is introduced into a solution consisting of 20,0 g of 1-(3,4-dimethoxyphenyl)-6-chloro-2-bromomagnesium naphthalene in 110 ml of tetrahydrofurane, made from 18,8 g of 1-(3,4-dimethoxyphenyl)-6-chloro-2-bromonaphthalene and 1,2 of magnesium. The introduction of carbon dioxide is continued for one hour after the exothermic reaction is finished. While cooling, 30 ml of 10% hydrochloric acid and thereafter 200 ml of water are then added dropwise, and the acid reaction solution is rendered alkaline with concentrated sodium hydroxide solution and extracted twice with 150 ml of ether each time. The aqueous phase is adjusted to pH 1 with 20% hydrochloric acid. The acid which precipitates is filtered off, washed with a small amount of water and dried in a vacuum drying cabinet at 80°. M.p. of the beige title compound >200°.

P.6: Preparation of 1-(3,4-dimethoxyphenyl)-6-chloro-2-bromonaphthalene (intermediate).

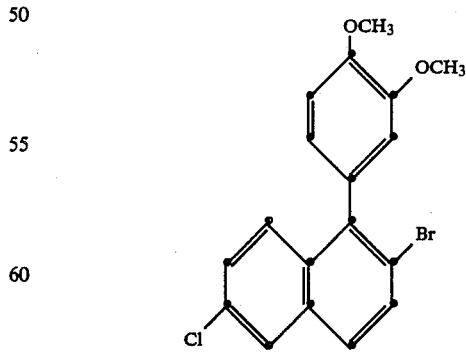

19.0 g of 1-(3,4-dimethoxyphenyl)-6-chloro-2-bromo-3,4-dihydronaphthalene dissolved in 100 ml of dichloroethane are added dropwise to 13.6 g of 2,3-dichloro-5,6-dicyano-1,4-benzoquinone in 300 ml of dichloroethane, and the reaction mixture is heated and kept under reflux for 16 hours.

When the reaction mixture has cooled, 300 ml of hexane are added thereto, the whole is filtered and the filtrate is concentrated by evaporation. For purification, the residue is chromatographed over a column of silica gel using ethyl acetate/hexane 2:1. The product is obtained in the form of a white powder. M.p. 117°–119°.

P.7: Preparation of 1-(3,4-dimethoxyphenyl)-6-chloro-2-bromo-3,4-dihydronaphthalene (intermediate).

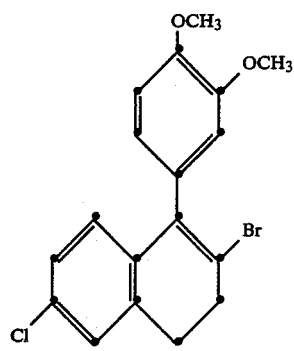

30.0 g of 1-(3,4-dimethoxyphenyl)-6-chloro-3,4-dihydronaphthalene are dissolved in 200 ml of methylene chloride and the solution is cooled to 0°. 31.2 g of pyridine hydrobromide perbromide are added in portions thereto over a period of 1½ hours at from 0° to 5°. When the addition is complete, the violet solution is stirred for 2 hours at 0°, 300 ml of 10% sodium bicarbonate solution are then added thereto, and the organic phase is separated off and washed with water, dried over sodium sulfate, filtered and concentrated by evaporation. The semi-crystalline product so obtained can be further reacted directly. Upon being left to stand for a longer period, the title compound crystallises out completely and can be digested in hexane. M.p. 92°–95°.

P.8: Preparation of 1-(3,4-dimethoxyphenyl)-6-chloro-3,4-dihydronaphthalene (intermediate).

43.0 g of 6-chloro-1-tetralone dissolved in 300 ml of tetrahydrofuran are added dropwise over a period of 1 hour at from 0° to a maximum of 5° to 96.4 g of 4-bromomagnesium veratrol, prepared from 9.6 g of magnesium and 86.8 g of 4-bromoveratrol, in 500 ml of tetrahydrofuran. The reaction mixture is subsequently stirred for 1 hour at room temperature and then for 5 hours under reflux. It is then cooled to room temperature and 150 ml of 10% hydrochloric acid and 500 ml of water are added thereto at reduced temperature. The reaction mixture is extracted three times with 250 ml of ether each time, and the organic phases are combined, washed twice with 150 ml of water each time, dried over sodium sulfate, filtered and concentrated by evaporation. In order to remove the elements of water completely, the oily residue is boiled under reflux for 2 hours in 150 ml of methanol/sulfuric acid (1:1). The olefin is then extracted from the cooled reaction solution three times with 250 ml of ether each time. The organic phases are combined, washed with water, dried over $Na_2SO_4$, filtered and concentrated by evaporation. For purification, the oily residue is subjected to column chromatography using ethyl acetate/hexane 1:2. The title compound is obtained in the form of a yellow oil.

The compounds listed in Tables 1 to 3 can be prepared analogously to Examples P.1 and P.4 or by one of the methods indicated hereinbefore.

TABLE 1

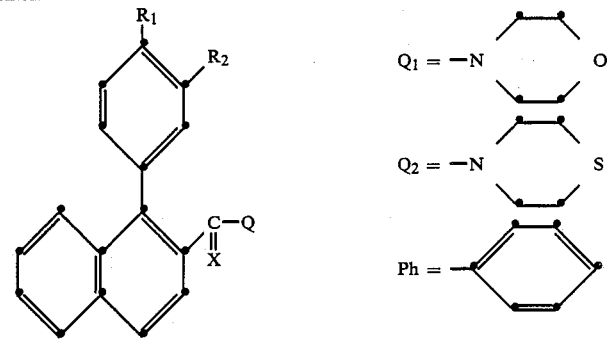

| Comp. no. | $R_1$ | $R_2$ | X | Q | phys. const. |
|---|---|---|---|---|---|
| 1.1. | $OCH_3$ | $OCH_3$ | O | $Q_1$ | m.p. 161–163° |
| 1.2. | $OCH_3$ | $OCH_3$ | O | $Q_2$ | m.p. 78–79° |
| 1.3. | $OC_2H_5$ | Cl | O | $Q_1$ | m.p. 76–81° |
| 1.4. | $OCH_3$ | $CH_3$ | O | $Q_2$ | |
| 1.5. | $OCH_3$ | $OC_2H_5$ | O | $Q_1$ | |
| 1.6. | $OCH_3$ | $OCH_3$ | S | $Q_1$ | m.p. 87–92° |

TABLE 1-continued

Structure: biphenyl-naphthalene with substituents $R_1$, $R_2$ on one ring and $C(=X)-Q$ on naphthalene.

$Q_1 = -N\overset{\frown}{\underset{\smile}{\phantom{X}}}O$ (morpholino)

$Q_2 = -N\overset{\frown}{\underset{\smile}{\phantom{X}}}S$ (thiomorpholino)

$Ph = $ phenyl

| Comp. no. | $R_1$ | $R_2$ | X | Q | phys. const. |
|---|---|---|---|---|---|
| 1.7. | OCH$_3$ | OCH$_3$ | O | —NHCH(CH$_3$)$_2$ | m.p. 181–186° |
| 1.8. | OCH$_3$ | OCH$_3$ | O | —N (heptamethyleneimino, 7-membered ring) | m.p. 60–65° |
| 1.9. | OC$_2$H$_5$ | Cl | O | Q$_2$ | m.p. 120–123° |
| 1.10. | OCH$_3$ | Cl | O | Q$_1$ | m.p. 76–82° |
| 1.11. | OC$_2$H$_5$ | OC$_2$H$_5$ | O | Q$_1$ | |
| 1.12. | OC$_2$H$_5$ | OCH$_3$ | O | Q$_2$ | |
| 1.13. | OCHF$_2$ | CH$_3$ | O | Q$_1$ | |
| 1.14. | OCH$_3$ | OCH$_3$ | O | —NH—C$_6$H$_4$—Cl | m.p. 190–193° |
| 1.15. | Cl | Cl | O | Q$_1$ | |
| 1.16. | OCH$_3$ | CH$_3$ | O | Q$_1$ | |
| 1.17. | OCH$_3$ | OCH$_3$ | O | —N(piperazinyl)N—CH$_3$ | m.p. 108–110° |
| 1.18. | CH$_3$ | CH$_3$ | O | Q$_1$ | |
| 1.19. | CH$_3$ | OCH$_3$ | O | Q$_1$ | |
| 1.20. | OCH$_3$ | Cl | O | Q$_2$ | m.p. 150–152° |
| 1.21. | Cl | CH$_3$ | O | Q$_1$ | |
| 1.22. | OCH$_3$ | OCH$_3$ | O | —NH-Ph | m.p. 158–163° |
| 1.23. | OCHF$_2$ | CH$_3$ | O | Q$_2$ | |
| 1.24. | —OCH$_2$O— | | O | Q$_1$ | m.p. 74–80° |
| 1.25. | —OCH$_2$O— | | O | —NH-Ph | |
| 1.26. | —OCH$_2$O— | | O | —N(2,6-dimethylmorpholino) | m.p. 118–134° |
| 1.27. | —OCH$_2$O— | | O | —NH—C$_6$H$_4$—Cl | |
| 1.28. | —OCH$_2$O— | | S | Q$_1$ | m.p. 168–170° |
| 1.29. | —OCH$_2$O— | | O | —N(CH$_3$)$_2$ | |
| 1.30. | —OCH$_2$O— | | O | —NHCH(CH$_3$)$_2$ | |

TABLE 1-continued

Structure: Naphthalene with phenyl substituent bearing R₁ and R₂; naphthalene bears C(=X)Q group.

$Q_1 = -N\overset{\frown}{\underset{\smile}{\phantom{X}}}O$ (morpholine)

$Q_2 = -N\overset{\frown}{\underset{\smile}{\phantom{X}}}S$ (thiomorpholine)

$Ph =$ phenyl

| Comp. no. | R₁ | R₂ | X | Q | phys. const. |
|---|---|---|---|---|---|
| 1.31. | —OCH₂O— | | O | —N(morpholine with 2,6-diCH₃) | m.p. 144–146° |
| 1.32. | —OCH₂O— | | O | —N(morpholine with CH₃, H) | m.p. 103–107° |
| 1.33. | —OCH₂CH₂O— | | O | Q₁ | m.p. 136–139° |
| 1.34. | —OCH₂CH₂O— | | O | —N(piperidine) | |
| 1.35. | —OCH₂CH₂O— | | O | Q₂ | m.p. 127–129° |
| 1.36. | —OCF₂O— | | O | Q₁ | |
| 1.37. | —OCF₂O— | | O | Q₂ | |
| 1.38. | —OCH₂O— | | S | Q₂ | |
| 1.39. | —OCH₂O— | | O | —N(piperidine) | m.p. 98–100° |
| 1.40. | —OCH₂O— | | O | Q₂ | m.p. 123–125° |
| 1.41. | —OCH₂O— | | NH | Q₁ | |
| 1.42. | —OCH₂O— | | S | Q₂ | |
| 1.43. | OCH₃ | OCH₃ | NH | Q₁ | |
| 1.44. | OCH₃ | OCH₃ | O | —N(CH₃)₂ | m.p. 147–148° |
| 1.45. | OCH₃ | OCH₃ | O | —N(piperidine) | m.p. 72–74° |
| 1.46. | OCH₃ | OCH₃ | O | —N(C₂H₅)₂ | m.p. 99–102° |
| 1.47. | OCHF₂ | OCH₃ | O | Q₁ | |
| 1.48. | CH₃ | Cl | O | Q₁ | |
| 1.49. | OCHF₂ | Cl | O | Q₁ | |
| 1.50. | OCH₃ | OCH₃ | O | —N(isoxazolidine) | |
| 1.51. | Cl | Cl | O | Q₂ | |
| 1.52. | N(CH₃)₂ | Cl | O | Q₁ | |

TABLE 1-continued

Structure: biphenyl-naphthalene with R₁, R₂ substituents and C(=X)-Q group.

Q₁ = morpholine (-N linked to O ring)
Q₂ = thiomorpholine (-N linked to S ring)
Ph = phenyl

| Comp. no. | R₁ | R₂ | X | Q | phys. const. |
|---|---|---|---|---|---|
| 1.53. | $NH_2$ | $CH_3$ | O | $Q_1$ | |
| 1.54. | $NH_2$ | Cl | O | $Q_1$ | |
| 1.55. | $OCH_3$ | $OCHF_2$ | O | $Q_1$ | |
| 1.56. | $OCH_3$ | $OCH_3$ | O | $-N(CH_2CH_2OCH_3)_2$ | |
| 1.57. | $OCH_3$ | Cl | O | $-NH-\text{C}_6\text{H}_4-Cl$ | m.p. 202–203° |
| 1.58. | $NH_2$ | $CH_3$ | O | $Q_2$ | |
| 1.59. | Cl | Cl | S | $Q_1$ | |
| 1.60. | $OCHF_2$ | $OCHF_2$ | O | $Q_1$ | |

TABLE 2

Structure: Ar-substituted naphthalene-2-carboxamide with morpholine-type ring containing X.

| Comp. no. | Ar | X | physical constant |
|---|---|---|---|
| 2.1. | 2,3,4-tri($OCH_3$)phenyl | O | m.p. 118–121° |
| 2.2 | 2,6-diCl-3-$NH_2$-phenyl | O | |
| 2.3. | 2,4-di($OCH_3$)phenyl | O | amorphous |
| 2.4. | 3,4-di($OCH_3$)phenyl | O | m.p. 132–133° |
| 2.5. | 2,4,5-tri($OCH_3$)phenyl | S | |
| 2.6. | 2,4,5-tri($OCH_3$)phenyl | O | |
| 2.7. | 3,4,5-tri($OCH_3$)phenyl | S | m.p. 140–141° |

TABLE 2-continued

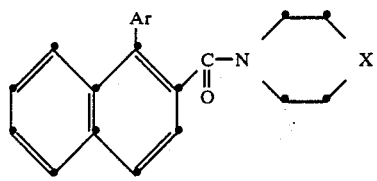

| Comp. no. | Ar | X | physical constant |
|---|---|---|---|
| 2.8. | 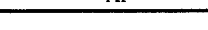 (2,4,5-tri-OCH₃ phenyl) | O | |
| 2.9. |  (2,4-diCl, 3-OCH₃ phenyl) | O | |

TABLE 3

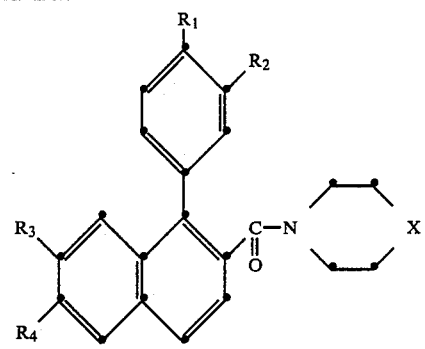

| Comp. no. | $R_1$ | $R_2$ | $R_3$ | $R_4$ | X | physical constant |
|---|---|---|---|---|---|---|
| 3.1. | OCH₃ | OCH₃ | H | Cl | O | m.p. 157–159° |
| 3.2. | OCH₃ | OCH₃ | OCH₃ | OCH₃ | O | |
| 3.3. | OCH₃ | OCH₃ | H | NH₂ | O | |
| 3.4. | OCH₃ | OCH₃ | H | Cl | S | |
| 3.5. | OCH₃ | OCH₃ | H | NH—COCH₃ | O | |
| 3.6. | OCH₃ | OCH₃ | —OCH₂O— | | O | |
| 3.7. | OCH₃ | OCH₃ | —OCH₂O— | | S | |
| 3.8. | OCH₃ | OCH₃ | H | Cl | CH₂ | |
| 3.9. | OCH₃ | OCH₃ | H | Cl | N—CH₃ | |
| 3.10. | OC₂H₅ | Cl | H | Cl | O | |
| 3.11. | OCH₃ | OC₂H₅ | H | Cl | O | |
| 3.12. | Cl | Cl | H | Cl | O | |
| 3.13. | OCHF₂ | OCHF₂ | H | Cl | O | |
| 3.14. | NH₂ | CH₃ | H | Cl | O | |
| 3.15. | —OCH₂O— | | H | Cl | O | |
| 3.16. | —OCH₂O— | | —OCH₂O— | | O | |
| 3.17. | —OCH₂O— | | H | Cl | S | |
| 3.18. | —OCH₂O— | | OCH₃ | OCH₃ | O | |
| 3.19. | —OCH₂O— | | H | Cl | S | |
| 3.20. | —OCH₂O— | | H | Cl | CH₂ | |
| 3.21. | —OCH₂O— | | H | NH₂ | O | |
| 3.22. | —OCH₂O— | | H | NHCOCH₃ | O | |
| 3.23. | —OCH₂O— | | H | Cl | N—CH₃ | |
| 3.24. | OCH₃ | OCH₃ | H | OCH₃ | O | |
| 3.25. | OCH₃ | OC₂H₅ | H | OCH₃ | O | |
| 3.26. | OCH₃ | OCH₃ | H | OCH₃ | S | |
| 3.27. | OCH₃ | OCH₃ | —OCF₂O— | | O | |
| 3.28. | —OCF₂O— | | H | Cl | O | |

2. FORMULATION EXAMPLES FOR ACTIVE INGREDIENTS OF FORMULA I (throughout, percentages are by weight)

| 2.1 Emulsifiable concentrates | (a) | (b) | (c) |
|---|---|---|---|
| a compound of Tables 1 to 3 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be obtained from such concentrates by dilution with water.

| 2.2. Solutions | (a) | (b) | (c) | (d) |
|---|---|---|---|---|
| a compound of Tables 1 to 3 | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160-190° C.) | — | — | 94% | — |

These solutions are suitable for application in the form of micro-drops.

| 2.3. Granulates | (a) | (b) |
|---|---|---|
| a compound of Tables 1 to 3 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4. Dusts | (a) | (b) |
|---|---|---|
| a compound of Tables 1 to 3 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| 2.5. Wettable powders | (a) | (b) | (c) |
|---|---|---|---|
| a compound of Tables 1 to 3 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7 to 8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

3. Biological Examples

Example 3.1

Action against Plasmopara viticola on vines (a) Residual protective action

Vine seedlings at the 4- to 5-leaf stage were sprayed with a spray mixture (0.02% active ingredient) prepared from a wettable powder formulation of the test compound. After 24 hours, the treated plants were infected with a sporangia suspension of the fungus. Fungus attack was evaluated after incubation for 6 days at 95–100% relative humidity and 20° C.

(b) Residual curative action

Vine seedlings at the 4- to 5-leaf stage were infected with a sporangia suspension of the fungus. After incubation for 24 hours in a humidity chamber at 95–100% relative humidity and 20° C., the infected plants were dried and sprayed with a spray mixture (0.02% active ingredient) prepared from a wettable powder formulation of the test compound. When the spray coating had dried, the treated plants were returned to the humidity chamber. Fungus attack was evaluated 6 days after infection.

Compounds of Tables 1 to 3 exhibited a very good fungicidal action against Plasmopara viticola on vines. In particular, compounds 1.1, 1.2, 1.6, 1.8, 1.24, 1.46 and 3.1 suppressed fungus attack completely (residual attack 0 to 5%).

Example 3.2

Action against Cercospora arachidicola on groundnut plants

Residual protective action

Groundnut plants 10–15 cm in height are sprayed with a spray mixture (0.02% active ingredient) prepared from a wettable powder formulation of the test compound, and infected 48 hours later with a conidia suspension of the fungus. The infected plants are incubated for 72 hours at about 21° C. and high humidity and then stood in a greenhouse until the typical leaf specks appear. Evaluation of the fungicidal action is made 12 days after infection and is based on the number and size of the specks.

Compared with untreated and infected control plants (number and size of the specks=100%). Cercospora attack on groundnut plants treated with compounds of the Tables is substantially reduced. Compounds 1.24 and 1.26 and others of Tables 1 to 3 inhibited the occurrence of specks almost completely (0 to 10%).

Example 3.3

Residual protective action against Venturia inaequalis on apple shoots

Apple cuttings with 10–20 cm long fresh shoots are sprayed with a spray mixture (0.02% active ingredient) prepared from a wettable powder formulation of the test compound. The treated plants are infected 24 hours later with a conidia suspension of the fungus. The plants are then incubated for 5 days at 90–100% relative humidity and stood in a greenhouse for a further 10 days at 20°–24° C. Scab attack is evaluated 15 days after infection. Compound 1.24 of Table 1 confines attack by the disease to less than 10%. On the other hand, attack on untreated and infected control shoots is 100%.

Example 3.4

Action against Erysiphe graminis on barley (a) Residual protective action

Barley plants about 8 cm in height are sprayed with a spray mixture (0.02% active ingredient) prepared from a wettable powder formulation of the test compound. The treated plants are dusted with conidia of the fungus after 3 to 4 hours. The infected barley plants are stood in a greenhouse at about 22° C. The fungus attack is evaluated after 10 days.

(b) Systemic action A spray mixture (0.02% active ingredient, based on the volume of the soil) prepared from a wettable powder formulation of the test compound is poured onto barley plants about 8 cm in height. Care is taken that the spray mixture does not come into contact with the parts of the plants above the soil. The treated plants are infected 48 hours later with a conidia suspension of the fungus. The infected barley plants are then stood in a greenhouse at about 22° C. and evaluation of fungus attack is made after 10 days.

Compounds of Tables 1 to 3 exhibited good activity against Erysiphe. For example, compounds 1.1, 1.2, 1.10, 1.24, 1.26, 1.31, 1.32, 1.40, 2.1 and 3.1 confined Erysiphe attack to from 0 to 5%. On the other hand, Erysiphe attack is 100% on untreated and infected control plants.

Example 3.5

Action against Phytophthora on tomato plants

Residual protective action

After a cultivation period of 3 weeks, tomato plants are sprayed with a spray mixture (0.02% active ingredient) prepared from a wettable powder formulation of the test compound. The treated plants are infected 24 hours later with a sporangia suspension of the fungus. Evaluation of the fungus attack is made after incubating the infected plants for 5 days at 90–100% relative humidity and 20° C.

Compounds of Tables 1 to 3 exhibited a lasting action (less than 20% fungus attack). Compounds 1.1, 1.6, 1.46 and 3.1, 3.4 and other preparations of Table 3 inhibited attack almost completely (0 to 5% attack).

What is claimed is:

1. 1-Aryl-2-naphthoylamines of formula I

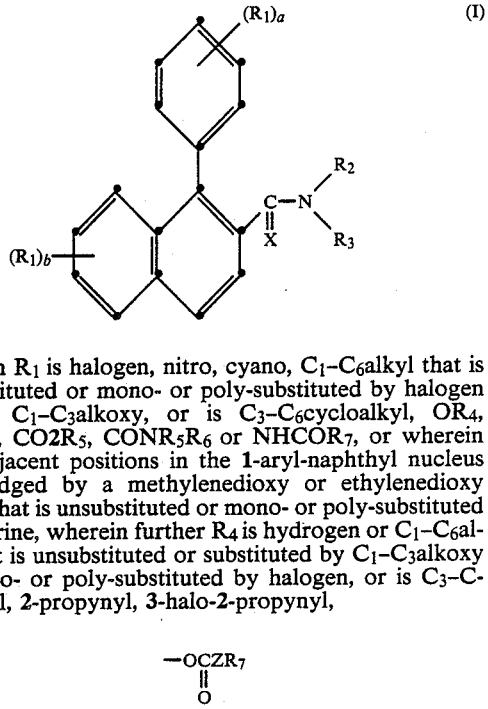

wherein $R_1$ is halogen, nitro, cyano, $C_1$–$C_6$alkyl that is unsubstituted or mono- or poly-substituted by halogen and/or $C_1$–$C_3$alkoxy, or is $C_3$–$C_6$cycloalkyl, $OR_4$, $NR_5R_6$, $CO_2R_5$, $CONR_5R_6$ or $NHCOR_7$, or wherein two adjacent positions in the 1-aryl-naphthyl nucleus are bridged by a methylenedioxy or ethylenedioxy group that is unsubstituted or mono- or poly-substituted by fluorine, wherein further $R_4$ is hydrogen or $C_1$–$C_6$alkyl that is unsubstituted or substituted by $C_1$–$C_3$alkoxy or mono- or poly-substituted by halogen, or is $C_3$–$C_4$alkenyl, 2-propynyl, 3-halo-2-propynyl,

or $COR_7$, each of $R_5$ and $R_6$, independently of the other, is H or $C_1$–$C_4$alkyl, $R_7$ is $C_1$–$C_4$alkyl and Z is O or NH, a and b denote the number of occupied positions in the respective 6-membered ring, and a is a number from 1 to 3 and b is a number from 0 to 3, the individual groups $R_1$ being identical or different when the sum of a and b is greater than 1, X is O, S or NH, $R_2$ and $R_3$ are together a $C_4$–$C_7$alkylene chain that together with the nitrogen atom may form a heterocycle that is unsubstituted or mono- or di-substituted by $C_1$–$C_4$ alkyl including the addition salts of compounds of formula I.

2. 1-Aryl-2-naphthoylamines according to claim 1, wherein $R_1$ is halogen, nitro, $C_1$–$C_6$alkyl, $C_3$–$C_6$cycloalkyl, or wherein two adjacent positions in the 1-aryl-naphthyl nucleus are bridges by methylenedioxy, ethylenedioxy or ethylenedioxy mono- or poly-substituted by flourine, or is $OR_4$ or $NR_5R_6$, mono- or poly-substituted by $OR_4$ or $NR_5R_6$, wherein $R_4$ is hydrogen or $C_1$–$C_3$alkyl that is unsubstituted or monosubstituted by $C_1$–$C_3$alkoxy or mono- to penta-substituted by halogen, each of $R_5$ and $R_6$, independently of the other, is H or $C_1$–$C_4$alkyl, a is the number 2 or 3, b is 0 or 1, and X is O or S, $R_2$ and $R_3$ are together a $C_4$–$C_7$alkylene chain that together with the nitrogen atom may form a heterocycle that is unsubstituted or mono- or di-substituted by $C_1$–$C_4$alkyl.

3. 1-Aryl-2-naphthoylamines according to claim 1, wherein $R_1$ is methoxy or methyl, a is the number 2 or 3 is the number 0, while X is sulfur.

4. A microbicidal composition containing a microbicidally effective amount of at least one of the compounds of formula I according to claim 1 as active ingredient, together with customary carriers and adjuvants.

5. A method of controlling phytopathogenic microbes, which comprises applying to the plant or to the local thereof a microbicidally effective amount of a compound of formula I according to claim 1.

6. A method according to claim 5, in which the microbes are Plasmopara, Venturia, Phytophtora, Cercospora or Erysiphe.

* * * * *